US010617833B2

(12) United States Patent
Alarcon

(10) Patent No.: US 10,617,833 B2
(45) Date of Patent: Apr. 14, 2020

(54) ELECTRONIC SMOKING DEVICE CONFIGURED FOR AUTOMATED ASSEMBLY

(71) Applicant: Fontem Holdings 4 B.V., Amsterdam (NL)

(72) Inventor: Ramon Alarcon, Los Gatos, CA (US)

(73) Assignee: Fontem Holdings 4 B.V., Amsterdam (NL)

( * ) Notice: Subject to any disclaimer, the term of this patent is extended or adjusted under 35 U.S.C. 154(b) by 0 days.

(21) Appl. No.: 14/915,175

(22) PCT Filed: Aug. 29, 2014

(86) PCT No.: PCT/US2014/053548
§ 371 (c)(1),
(2) Date: Feb. 26, 2016

(87) PCT Pub. No.: WO2015/031836
PCT Pub. Date: Mar. 5, 2015

(65) Prior Publication Data
US 2016/0198770 A1    Jul. 14, 2016

Related U.S. Application Data

(60) Provisional application No. 61/871,639, filed on Aug. 29, 2013.

(51) Int. Cl.
*A61M 15/06* (2006.01)
*H05B 1/02* (2006.01)
(Continued)

(52) U.S. Cl.
CPC ........... *A61M 15/06* (2013.01); *A24F 47/008* (2013.01); *A61M 11/042* (2014.02);
(Continued)

(58) Field of Classification Search
CPC ... A24F 47/008; A61M 11/042; A61M 15/06; A61M 2016/0021; A61M 2016/0027;
(Continued)

(56) References Cited

U.S. PATENT DOCUMENTS 3,111,396 A    11/1963   Ball et al.
8,833,364 B2   9/2014    Buchberger
(Continued)

FOREIGN PATENT DOCUMENTS

CN    1968822 A      5/2007
CN    101518361 A    9/2009
(Continued)

OTHER PUBLICATIONS

Chinese search report, corresponding to Applicant's CN application No. 2014800532641, dated Aug. 3, 2018.
(Continued)

*Primary Examiner* — Dana Ross
*Assistant Examiner* — Joseph W Iskra
(74) *Attorney, Agent, or Firm* — Dykema Gossett PLLC

(57) ABSTRACT

According to one non-limiting example of the disclosure, a system, a method, a device and a computer program are provided for the automated manufacture of electronic cigarettes. The apparatus comprises an electronic smoking device for delivering a vaporized liquid comprising a frame (200), an air flow path (122), an air inlet, a container (140) for storing a smoking liquid, and a circuit. At least a part of the circuit comprising traces printed on the frame (1306). The method comprises a frame, that can include slots configured for mating with and containing various components of the electronic smoking device. The computer readable medium comprises sections or segments of code that, when executed on a computer, cause the processes described (Continued)

herein to be carried, such as, for example, the process of assembling the electronic smoking device.

20 Claims, 14 Drawing Sheets

(51) Int. Cl.
*H05B 3/14* (2006.01)
*A61M 11/04* (2006.01)
*A24F 47/00* (2020.01)
*A61M 16/00* (2006.01)

(52) U.S. Cl.
CPC ......... *H05B 1/0202* (2013.01); *H05B 1/0244* (2013.01); *H05B 3/141* (2013.01); *A61M 2016/0021* (2013.01); *A61M 2016/0027* (2013.01); *A61M 2016/0039* (2013.01); *A61M 2205/3306* (2013.01); *A61M 2205/3317* (2013.01); *A61M 2205/3569* (2013.01); *A61M 2205/3584* (2013.01); *A61M 2205/3592* (2013.01); *A61M 2205/3653* (2013.01); *A61M 2205/50* (2013.01); *A61M 2205/52* (2013.01); *A61M 2205/581* (2013.01); *A61M 2205/582* (2013.01); *A61M 2205/583* (2013.01); *A61M 2205/8206* (2013.01)

(58) Field of Classification Search
CPC .. A61M 2016/0039; A61M 2205/3306; A61M 2205/3317; A61M 2205/3569; A61M 2205/3584; A61M 2205/3592; A61M 2205/3653; A61M 2205/50; A61M 2205/52; A61M 2205/581; A61M 2205/582; A61M 2205/583; A61M 2205/8206; H05B 1/0202; H05B 1/0244; H05B 3/141
USPC ................ 392/404; 131/328–330, 273, 194; 128/200.14, 200.23, 201.13, 202.21, 128/203.12, 203.16–203.17, 204.13, 128/204.17
See application file for complete search history.

(56) References Cited

U.S. PATENT DOCUMENTS

| | | |
|---|---|---|
| 2009/0095311 A1 | 4/2009 | Han |
| 2011/0021255 A1 | 1/2011 | Kim et al. |
| 2011/0226236 A1* | 9/2011 | Buchberger ......... A61M 11/041 128/200.23 |
| 2011/0265806 A1* | 11/2011 | Alarcon ................. A24F 47/00 131/273 |
| 2011/0277757 A1 | 11/2011 | Terry et al. |
| 2013/0050571 A1 | 2/2013 | Tam |
| 2013/0170171 A1* | 7/2013 | Wicker ............... H01L 21/4846 361/809 |
| 2014/0261491 A1 | 9/2014 | Hawes |
| 2016/0176564 A1 | 6/2016 | Garthaffner |

FOREIGN PATENT DOCUMENTS

| | | |
|---|---|---|
| CN | 201379072 Y | 1/2010 |
| CN | 101964446 A | 2/2011 |
| CN | 102264420 A | 11/2011 |
| CN | 102886973 A | 1/2013 |
| CN | 102957854 A | 3/2013 |
| CN | 102970885 A | 3/2013 |
| CN | 103263085 A | 8/2013 |
| WO | 2007131449 A1 | 11/2007 |
| WO | 201137453 A2 | 3/2011 |
| WO | 2016007516 A1 | 1/2016 |

OTHER PUBLICATIONS

Second Chinese Office Action (CN 201480053264.1) dated May 15, 2019 (33 pages).
Chinese Search Report (CN 201480053264.1) dated May 15, 2019 (3 pages).

* cited by examiner

ELECTRONIC SMOKING DEVICE CONFIGURED FOR AUTOMATED ASSEMBLY

BACKGROUND OF THE PRESENT DISCLOSURE

1. Field of the Present Disclosure

The present disclosure is directed to an electronic smoking device, and particularly to an electronic smoking device configured to be automatically assembled.

2. Related Art

Electronic cigarettes are a popular alternative to traditional tobacco based cigarettes that must be burned in order to generate smoke for inhalation. Electronic cigarettes provide a vapor for inhalation, but do not contain certain byproducts of combustion that may be harmful to human health. However, electronic cigarettes are a relatively new invention and current systems have some limitations. For example, electronic cigarettes have a non-uniform rate of vaporization and may sometimes produce an inconsistent quality of vapor. This may be due in part to the use of a wick that transports liquid from a disposable cartridge to the vaporizing element. The "wicking" method of fluid transport is a relatively slow method and therefore limits the rate at which the user can smoke the cigarette. Moreover, the wick construction is more difficult to assemble in an automated manufacturing process.

Furthermore, existing electronic cigarettes are manually assembled from constituent components. This assembly process tends to be labor intensive and susceptible to human error, potentially resulting in inconsistencies in product quality and workmanship.

Accordingly, there is a need for an improved electronic cigarette that can be manufactured automatically, as well as a process for assembly the electronic cigarette with minimal human intervention.

SUMMARY OF THE DISCLOSURE

According to one non-limiting example of the disclosure, a system, a method, a device and a computer program are provided for the automated manufacture of electronic cigarettes.

Additional features, advantages, and embodiments of the disclosure may be set forth or apparent from consideration of the detailed description and drawings. Moreover, it is to be understood that the foregoing summary of the disclosure and the following detailed description and drawings are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF THE DISCLOSURE

Figure 1:
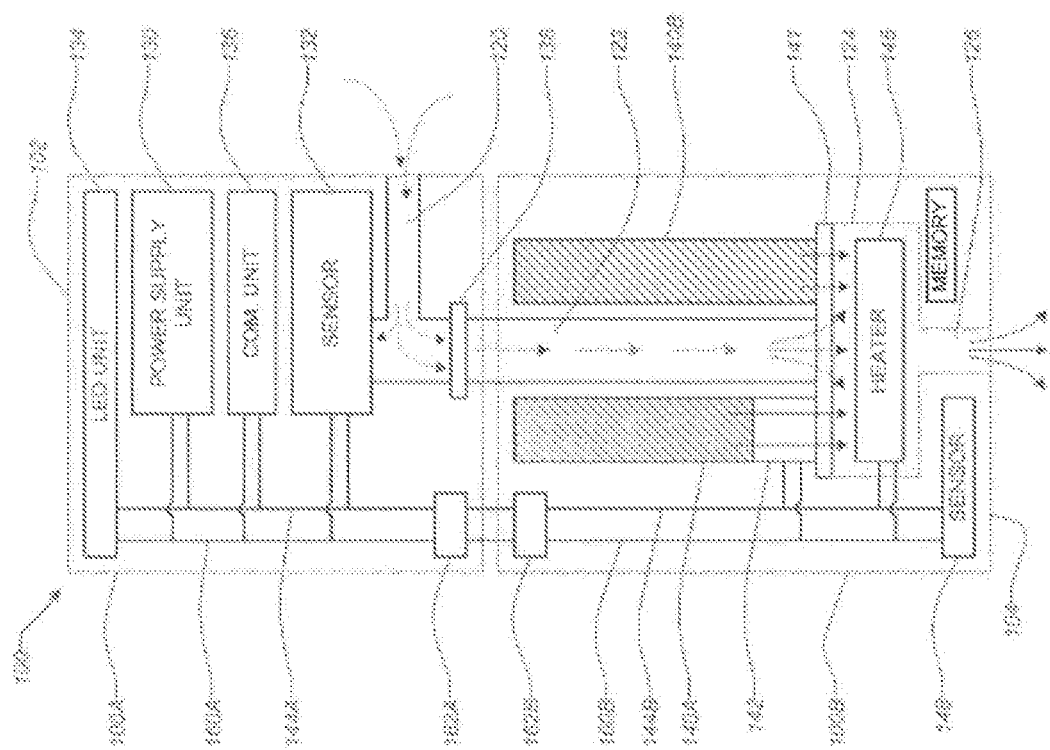
FIG. 1 shows internal components of an example of an electronic smoking device.

The embodiments of the disclosure and the various features and advantageous details thereof are explained more fully with reference to the non-limiting embodiments and examples that are described and/or illustrated in the accompanying drawings and detailed in the following attached description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

FIG. 1 shows a structural overview of an electronic smoking device (ESD) 100 constructed according to the principles of the disclosure. The ESD 100 may be disposable or reusable. The ESD 100 may have an elongated shape with a first end 102 and a second end 104, and may be similar to a conventional cigarette shape. Other non-conventional cigarette shapes are also contemplated. For example, the ESD 100 may have a smoking pipe shape or the like.

The ESD 100 may include an air inlet 120, an air flow path 122, a vaporizing chamber 124, a vapor outlet 126, a power supply unit 130, a sensor 132, a container 140, a dispensing control device 141, an atomizer 146 (such as, e.g., a heater, a piezo surface, an ultrasonic device, or the like), and/or the like. The air inlet may alternatively be located at first end 102, as shown at 120'. Further, the ESD 100 may include a controller, such as, e.g., microcontroller, microprocessor, a custom analog circuit, an application-specific integrated circuit (ASIC), a programmable logic device (PLD) (e.g., field programmable gate array (FPGA) and the like) and/or the like and basic digital and analog circuit equivalents thereof. The air inlet 120 may extend from, for example, are exterior surface of a housing of the ESD 100. The air flow path 122 may be connected to the air inlet 120 and extending to the vaporizing chamber 124. The vapor outlet 126 may be connected to the vaporizing chamber 124. The vapor outlet 126 may be formed at the second end 104 of the ESD 100 and connected to the vaporizing chamber 124. When a user sucks the second end 104 of the ESD 100, air outside the air inlet 120 may be pulled in and moved to the vaporizing chamber 124 via the air flow path 122, as indicated by the dotted arrows in FIG. 1. The atomizer 146 may be a solid state heater or the like, and located in the vaporizing chamber 124. The container 140 may contain the smoking liquid and connected to the vaporizing chamber 124. The container 140 may have an opening connected to the vaporizing chamber 124. The container 140 may be a single container or a group of containers that are connected to or separated from each other. In accordance with some principles of the disclosure, a group of containers 140 may be provided, each having its own selectively tuned screen 141. In some aspects, the selectively tuned screens 141 may enable user to create a desired vapor, for example, with more or less nicotine or more or less pg/vg to adjust the appearance of the vapor.

The dispensing control device 141 may be connected to the container 140 in order to control flow of the smoking liquid from the container 140 to the vaporizing chamber 124. When the user is not smoking the ESD 100, the dispensing control device 141 may not dispense the smoking liquid from the container 140. The dispensing control device 141 may not need any electric power from, for example, the power supply unit 130 and/or the like, for operation.

In one aspect, the dispensing control device 141 may be a micro liquid screen 141, such as, e.g., micro-etched screen, micromesh screen and the like. The micro liquid screen 141 may have a micro aperture pattern, which may keep the smoking liquid from seeping out therethrough by a surface tension and/or the like when the ESD 100 is not being used or when an air flow within the vaporizing chamber 124 is minimal. When an external force is applied, the smoking liquid may flow through the micro liquid screen 141. For example, when the user sucks the second end 104 of the ESD 100, an air flow may be formed in the vaporizing chamber 124 from the air flow path 122 to the vapor outlet 126, which may temporarily break the surface tension of the smoking liquid formed at the micro aperture pattern of the at the micro liquid screen 141. When the air flow is discontinued, the surface tension may be reestablished at the micro aperture pattern of the micro liquid screen 141, and the smoking liquid may stop being drawn therethrough. The micro liquid screen 141 may have a circular shape with a diameter larger than that of the container 140. One side of the micro liquid screen 141 may face an opening of the container 140 and the air flow path 122, and the other side may face the vaporizing chamber 124 and the atomizer 146. Micro liquid screen 141 may also be configured as an exit surface of a porous ceramic element. Furthermore, the exit surface may be a resistive coated surface forming a heating surface/element integral to micro liquid screen 141.

The micro liquid screen 141 may be a passive device that does not require electric power and a control signal. Other passive or active filtering/screening devices are also contemplated for the dispensing control device 141. For example, the dispensing control device may be a semi-active dispensing device, such as, e.g., electro-permeable membrane or the like, which does not allow a liquid to flow therethrough unless an electrical field is applied thereto. Alternatively or additionally, an active dispensing device 142 may be connected to the container 140 in order to consistently dispense substantially the same amount of smoking liquid to the vaporizing chamber 124 each time.

The power supply unit 130 may be connected to one or more components that require electric power, such as, e.g., the sensor 132, the active dispensing device 142, the atomizer 146, and the like, via a power bus 160. The power supply unit 130 may include a battery (not shown), such as, e.g., a rechargeable battery, a disposable battery and/or the like. The power unit 130 may further include a power control logic (not shown) for carrying out charging of the battery, detecting the battery charge status, performing power save operations and/or the like. The power control logic may be, for example, in the form of a microcontroller. The power supply unit 130 may include a non-contact inductive recharging system such that the ESD 100 may be charged without being physically connected to an external power source. A contact charging system is also contemplated.

The sensor 132 may be configured to detect the user's action for smoking, such as, e.g., sucking of the second end 104 of the ESD 100, touching of a specific area of the ESD 100 and/or the like. When the user's action for smoking is detected, the sensor 132 may send a signal to other components via a data bus 144. For example, the sensor 132 may send a signal to turn on the atomizer 146. Also, the sensor 132 may send a signal to the active dispensing device 142 (if utilized) to dispense a predetermined amount of the smoking liquid to the vaporizing chamber 124. When the smoking liquid is dispensed from the container 140 and the atomizer 146 is turned on, the smoking liquid may be mixed with the air from the flow path 122 and vaporized by the heat from the atomizer 146 within the vaporizing chamber 124. The resultant vapor may be pulled out from the vaporizing chamber 124 via the vapor outlet 126 for the user's oral inhalation, as indicated by solid arrows in FIG. 1. In order to prevent the vapor generated in the vaporizing chamber 124 from flowing towards the air inlet 120, the air flow path 122 may include a backflow prevention screen or filter 138.

When the user's action for smoking is stopped, the sensor 132 may send another signal to turn off the atomizer 146, the active dispensing device 142, and/or the like, and vaporization and/or dispensing of the smoking liquid may stop immediately. In an alternative embodiment, the sensor 132 may be connected only to the power supply unit 130. When the user's action for smoking is detected, the sensor 132 may send a signal to the power supply unit 130. In response to the signal, the power supply unit 130 may turn on other components, such as, e.g., the atomizer 146 and the like, to vaporize the smoking liquid.

In an embodiment, the sensor 132 may be an air flow sensor. For example, the sensor 132 may be connected to the air inlet 120, the air flow path 122, and/or the like, as shown in FIG. 1. When the user sucks the second end 104 of the ESD 100, some of the air pulled in from the air inlet 120 may be moved towards the sensor 132, which may be detected by the sensor 132. Additionally or alternatively, a capacitive sensor 148 may be used to detect the user's touching of a specific area of the housing 100. For example, the capacitive sensor 148 may be formed at the second end 104 of the ESD 100. When the ESD 100 is moved to the user's mouth and the user's lip touches the second end 104, a change in capacitance may be detected by the capacitive sensor 148, and the capacitive sensor 148 may send a signal to activate the atomizer 146 and the like. Other types of sensors are also contemplated for detecting the user's action for smoking, including, for example, an acoustic sensor, a pressure sensor, a touch sensor, an optical sensor, a Hall Effect sensor, an electromagnetic field sensor, and/or the like.

The ESD 100 may further include a communication unit 136 for wired (e.g., SPI (Serial Peripheral Interface) or the like) and/or wireless communications with other devices, such as, e.g., a pack for the ESD 100, a computer and/or the like. The communication unit 136 may also connect the ESD 100 to a wired network (e.g., LAN, WAN, Internet, Intranet and/or the like) and/or a wireless network (e.g., a WIFI network, a Bluetooth network, a cellular data network and/or the like). For example, the communication unit 136 may send usage data, system diagnostics data, system error data, and/or the like to the pack, the computer, and/or the like. To establish wireless communication, the communication unit 136 may include an antenna and/or the like. The ESD 100 may include a terminal 162 for wired communication. In accordance with some principles of the disclosure, the sensor 132 may include memory for storing operating instructions, execution parameters, and/or data that may be generated during the course of operation. Alternatively, where the heater and juice storage area are separable from the power supply unit and sensor 132, additional memory may be incorporated into the heater and juice storage portion. The communication unit 136 may also be configured to communicate with the additional memory via terminal 162 to exchange information such as, for example, the manufacturing date, heater temperature set point data, serial number, and the like. Such information may be stored in an electrically programmable memory device such as an EPROM, EEPROM, flash memory, or the like. In accordance with some principles of the disclosure, the information stored in the additional memory may be represented by the value of one or more resistors electrically connected to the terminal 162. The terminal 162 may be connected to another terminal, such as, e.g., a cigarette connector of the pack or the like, in order to exchange data. The terminal 162 may also be used to receive power from the pack 200 or other external power source and recharge the battery in the power supply unit 130.

The ESD 100 may further include one or more user interface devices, such as, e.g., an LED unit 134, a sound generator (not shown), a vibrating motor (not shown), and/or the like. The LED unit 134 may be connected to the power supply unit 130 via the power bus 160A and the data bus 144A, respectively. The LED unit 134 may provide a visual indication when the ESD 100 is operating. Additionally, when there is an issue and/or problem within the ESD 100, the integrated sensor/controller circuit 132 may control the LED unit 134 to generate a different visual indication. For example, when the container 140 is almost empty or the battery charge level is low, the LED unit 134 may blink in a certain pattern (e.g., blinking with longer intervals for thirty seconds). When the atomizer 146 is malfunctioning, the atomizer 146 may be disabled and control the LED unit 134 may blink in a different pattern (e.g., blinking with shorter intervals for one minute). Other user interface devices may be used to show a text, image, and/or the like, and/or generate a sound, a vibration, and/or the like.

In the ESD 100 shown in FIG. 1, the sensor 132 alone may not be able to control the user interface devices, the communication unit 136, the sensors 132 and 148 and/or the like. Furthermore, it may not be possible to carry out more complex and sophisticated operations with the sensor 132 alone. Thus, as noted above, a controller, such as, e.g., microcontroller, microprocessor, a custom analog circuit, an application-specific integrated circuit (ASIC), a programmable logic device (PLD) (e.g., field programmable gate array (FPGA) and the like) and/or the like and basic digital and analog circuit equivalents thereof, may be included the ESD 100.

Figure 2:
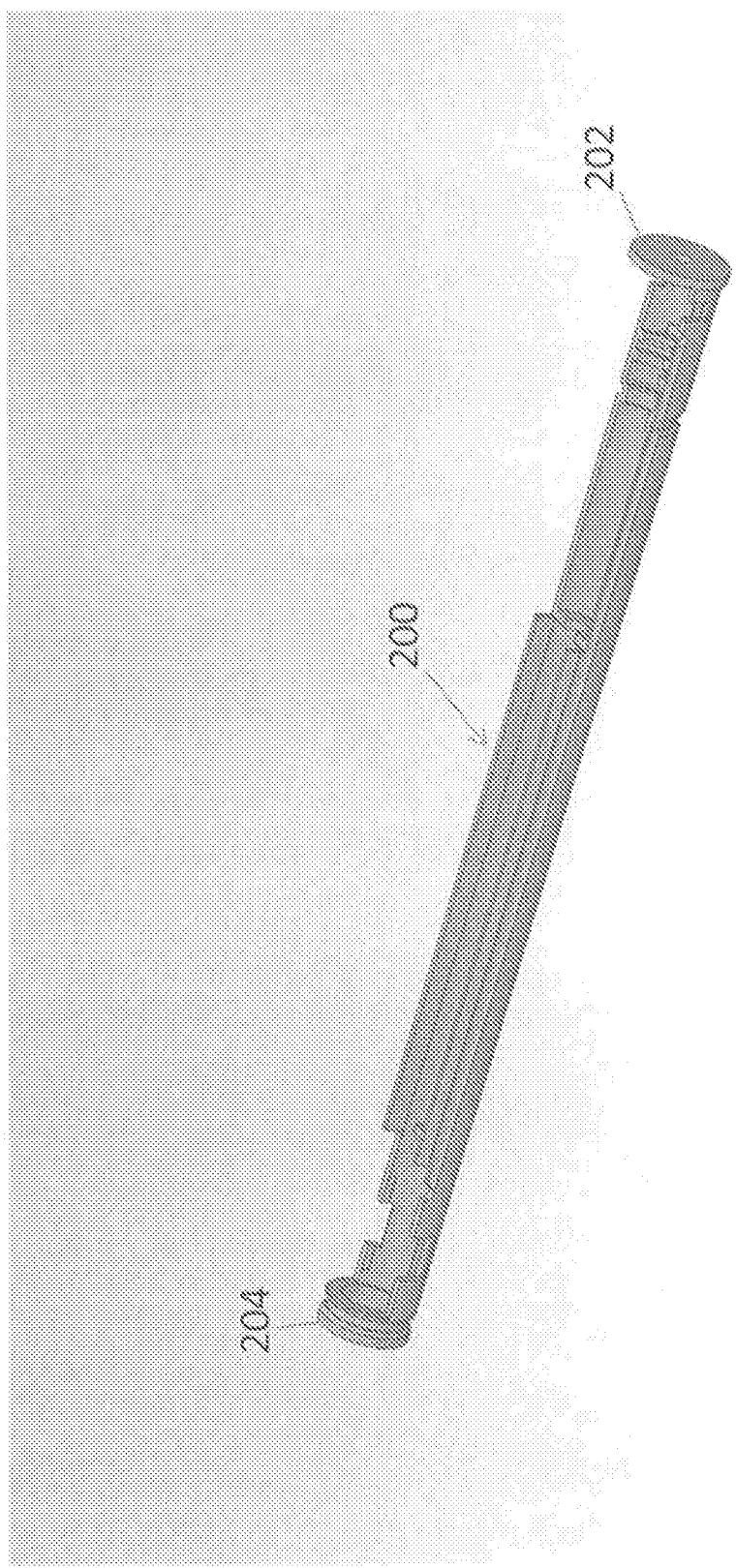
FIGS. 2-12 show an example modular construction of an electronic smoking device.

FIG. 2 shows an example of an open frame 200 that may house, for example, the ESD components described above with respect to FIG. 1. The open frame 200 is configured for easy, top-down or bottom-up assembly, depending on the configuration of the equipment used to assemble the ESD. As seen in FIG. 2, the open frame 200 may include integrally formed first and second endpoints 202 and 204, respectively. In addition, open frame 200 may be configured with openings/slots specifically sized to securely contain the elements of the ESD, as will be described in more detail below.

Figure 3:
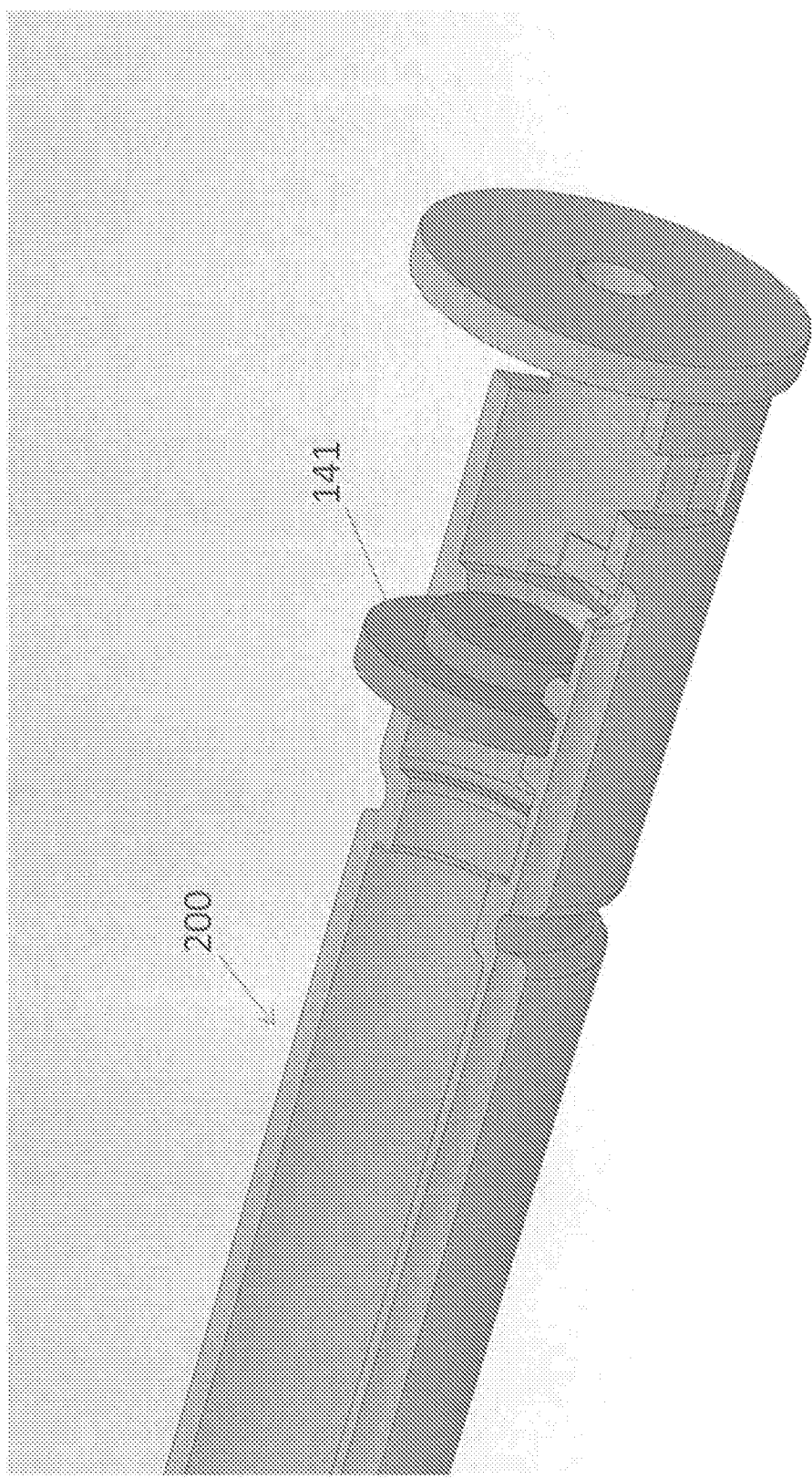

As seen in FIG. 3, open frame 200 may include a slot for containing dispensing control device 141. Dispensing control device 141 may be configured with holes having a diameter between 0.008" and 0.020", for example, to allow the liquid to flow through the dispensing control device when air is sucked though an inner tube. The viscosity of the liquid may be such that the liquid may be prevented from leaking though small holes when no airflow is present.

Figure 4:
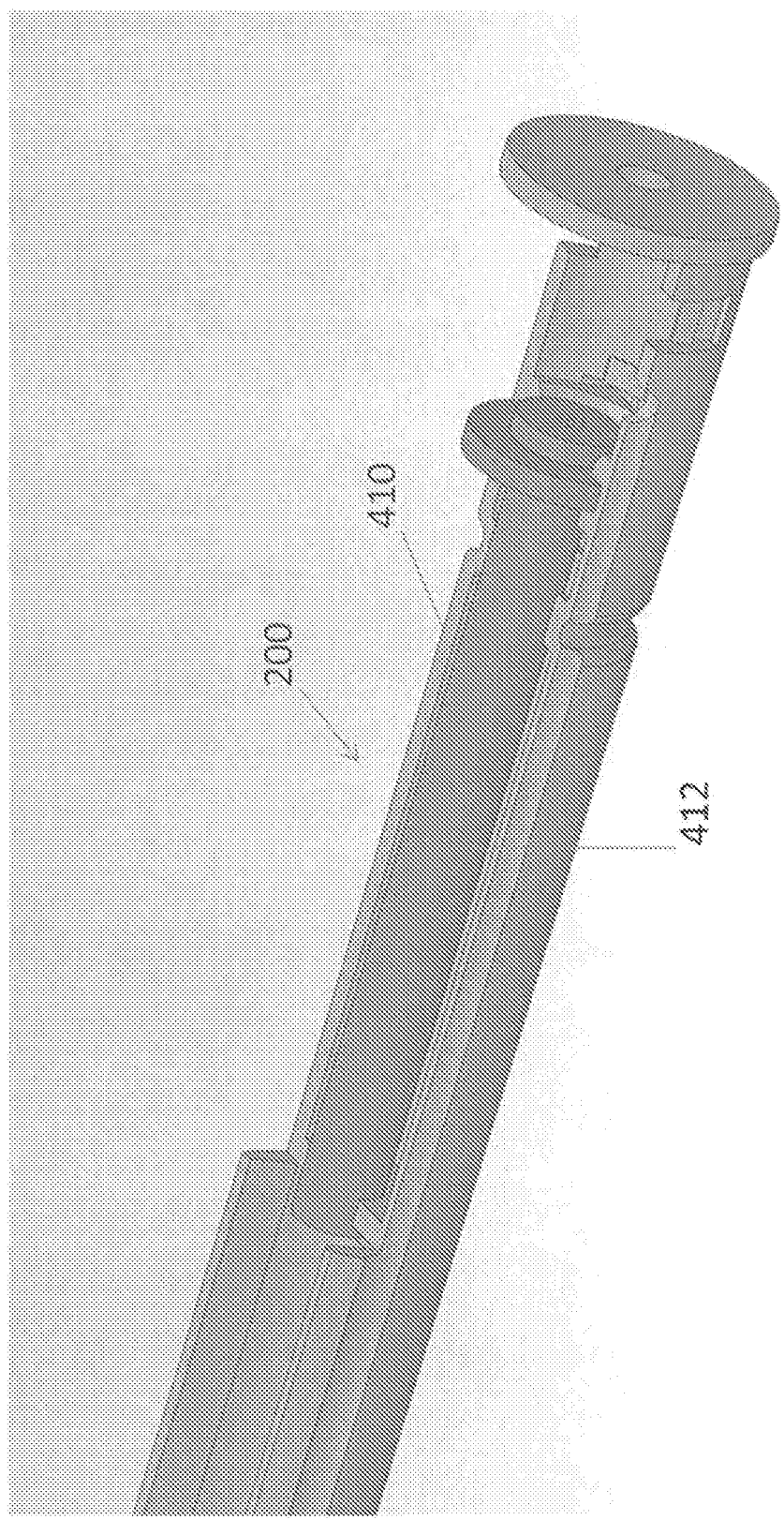
Figure 5:
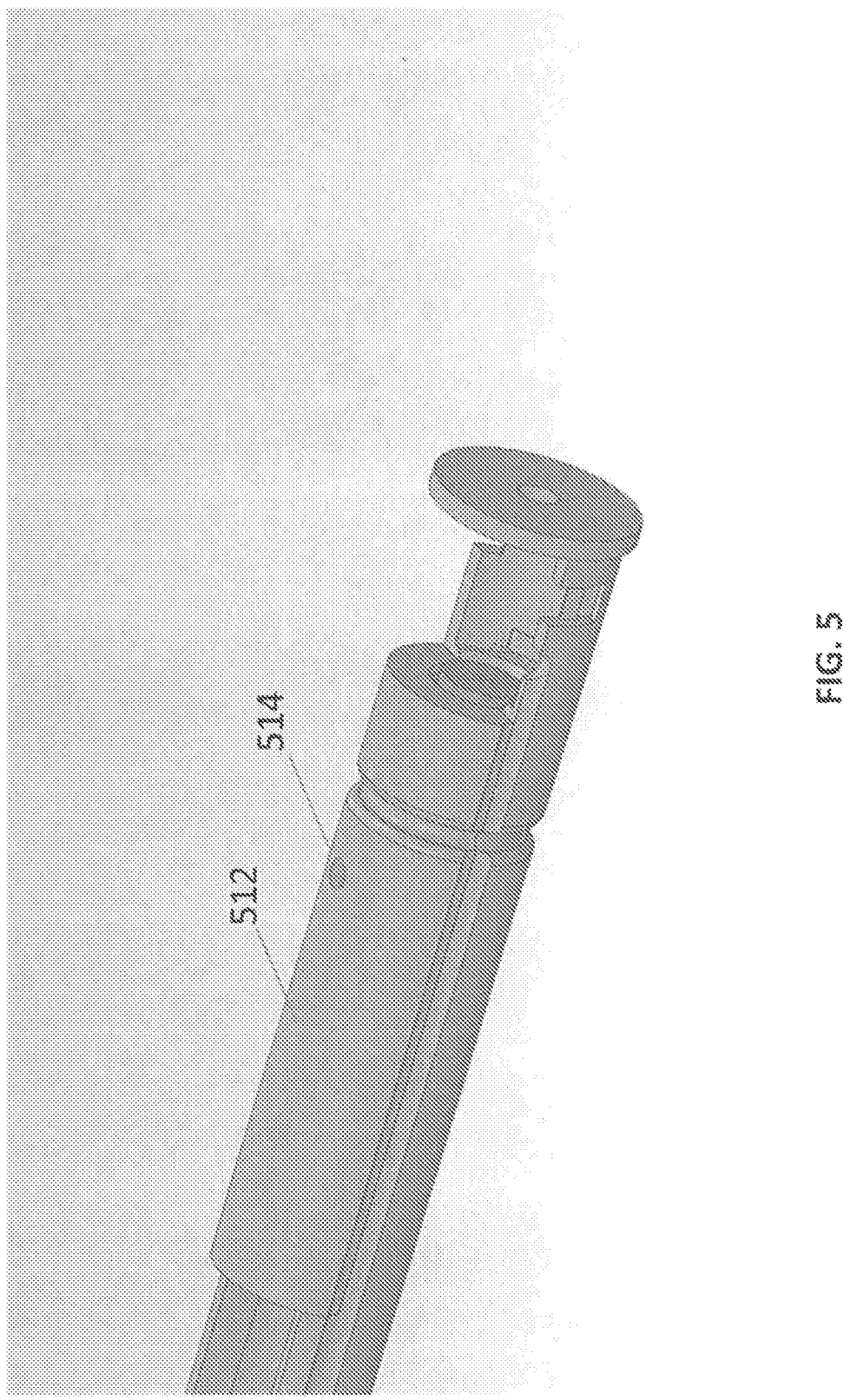

As seen in FIG. 4, open frame 200 includes a slot 410 for containing an air flow tube 412. The slot 410 may be configured such that air flow tube 412 fits snugly therein, and forms a chamber for the smoking liquid to surround the air flow tube 412. Ambient air may be drawn through the center of the air flow tube 412. As seen in FIG. 5, a liquid chamber cover 512 may be ultrasonically welded or glued to the open frame 200 to form a liquid tight chamber over or surrounding the air flow tube 412 and smoking liquid. The liquid chamber cover 512 may include a fill port 514 for filling the smoking liquid into the liquid chamber. In accordance with some principles of the disclosure, components such as the air flow tube 412 may be integrally molded.

Figure 6:
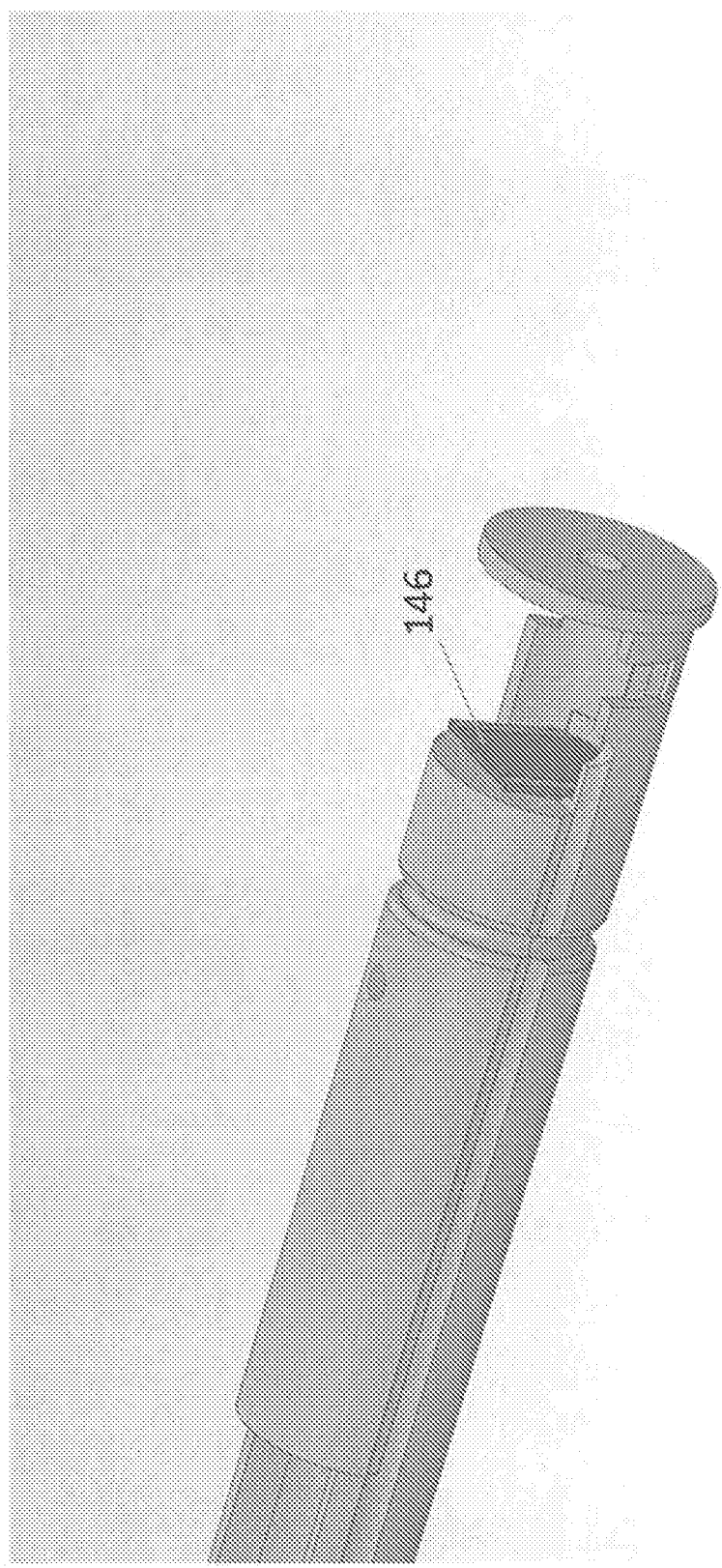
Figure 7:
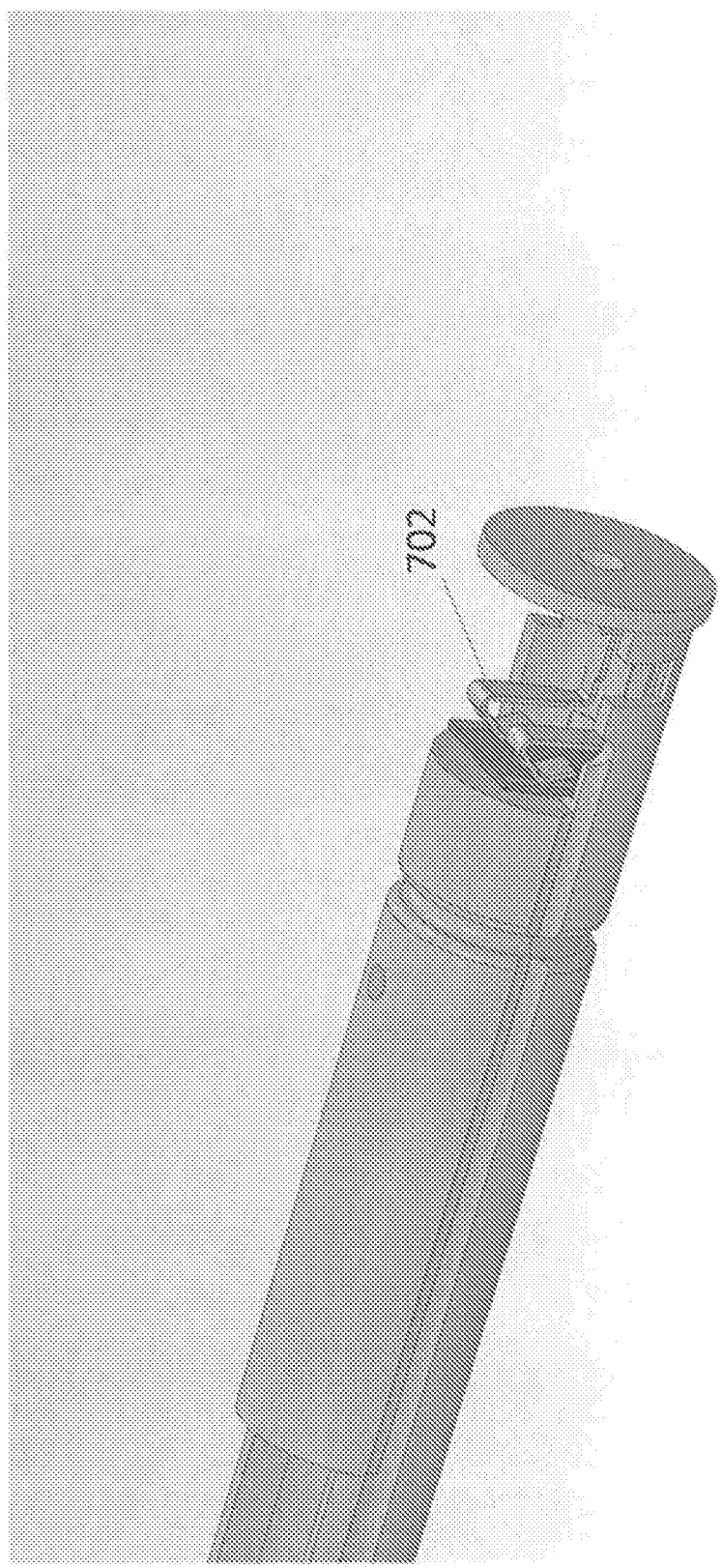
Figure 8:
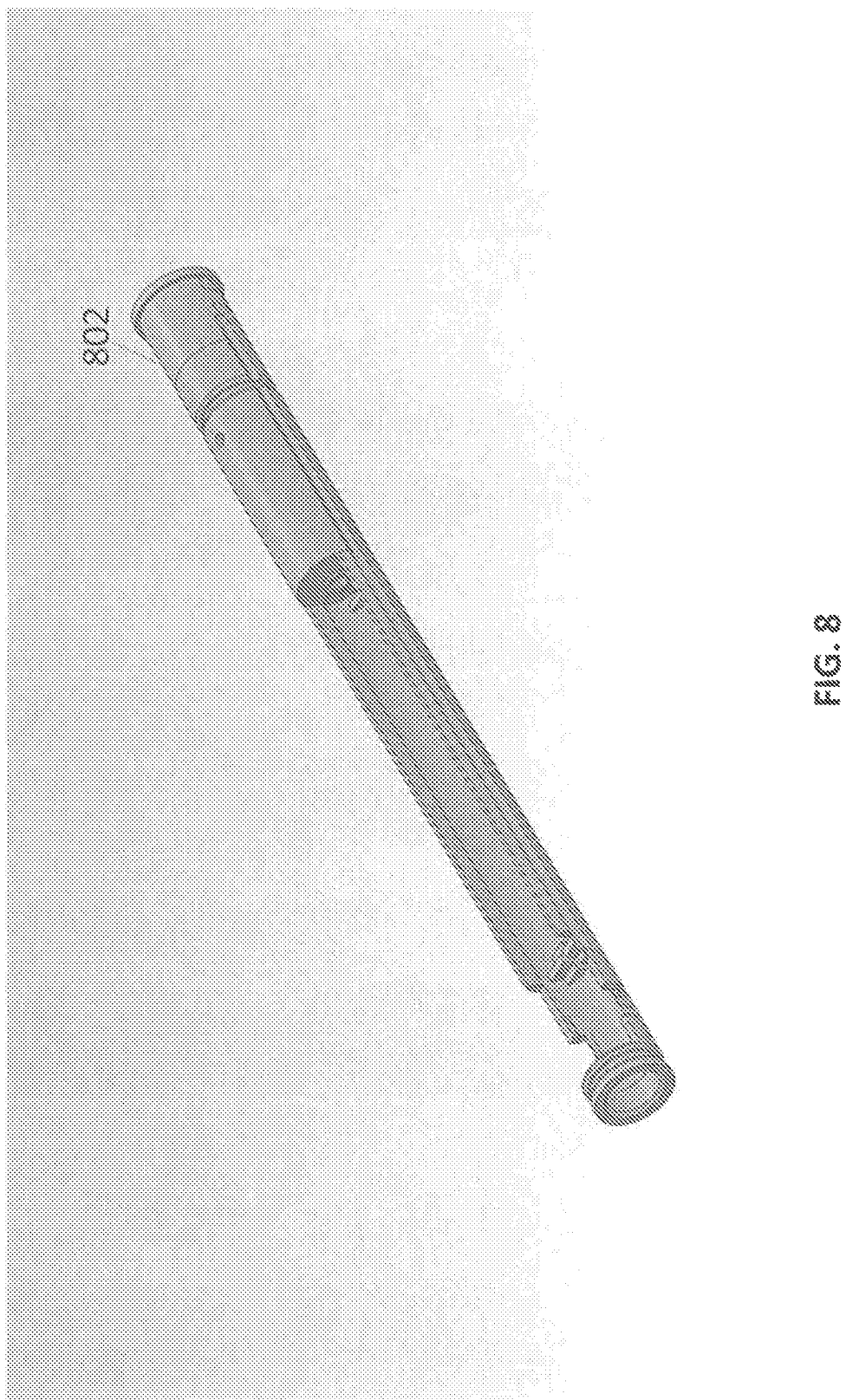

Open frame 200 may also include a slot for containing atomizer 146, as seen in FIG. 6. Atomizer 146 may comprise a ceramic non-porous (or porous) substrate having resistive elements deposited thereon. Open frame 200 may also include a slot for containing plated electrical contacts 702, as shown in FIG. 7. Contacts may alternatively be printed on the open frame 200 or insert molded to form integral contacts. A cap 805 that can be affixed (e.g., snapped in place) to the open frame 200 may be provided to hold in the components of the heater section, as shown in FIG. 8. In accordance with some principles of the disclosure, a memory device may be placed in proximity to the heater and in contact with one or more plated electrical contacts.

Figure 9:
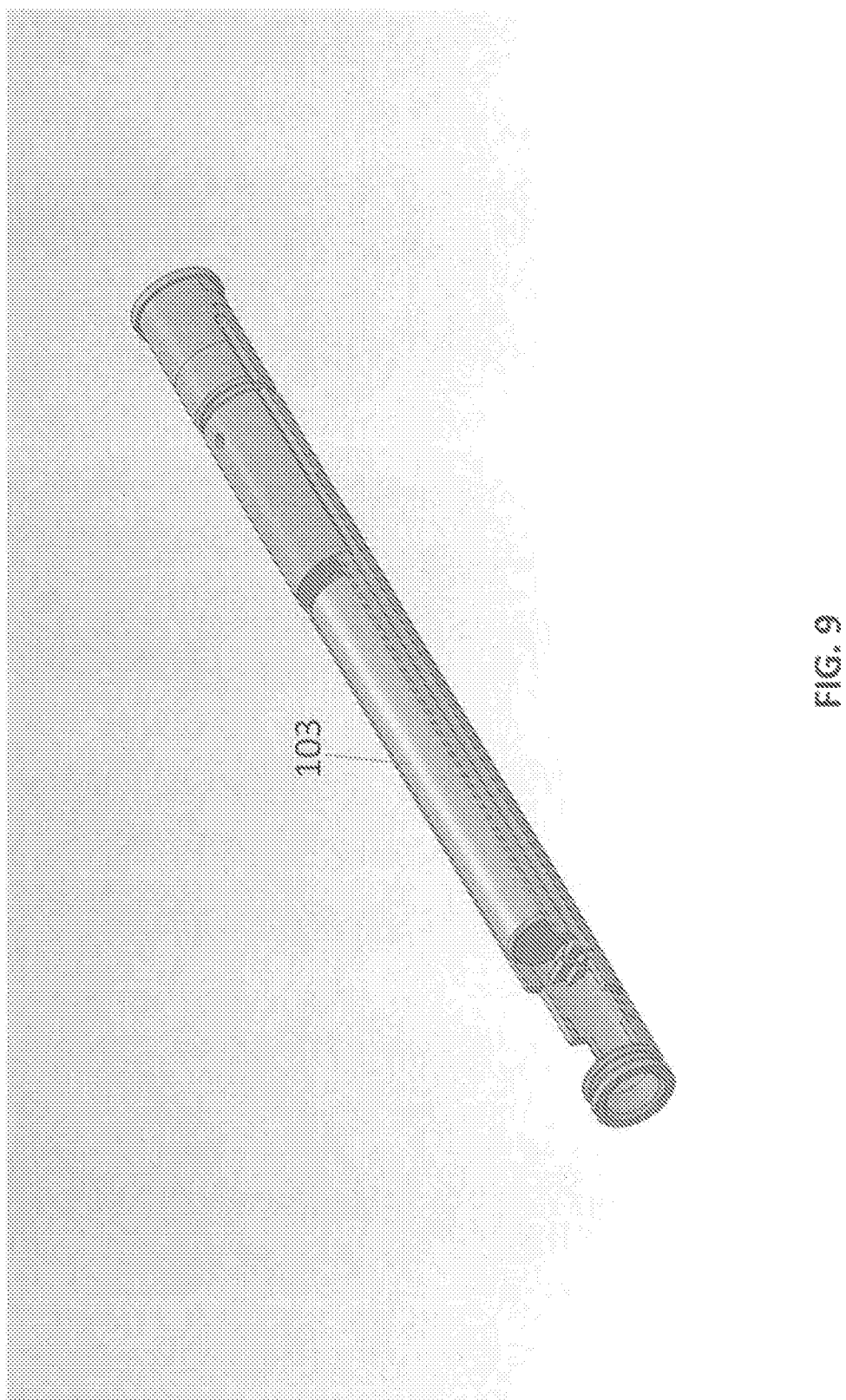
Figure 10:
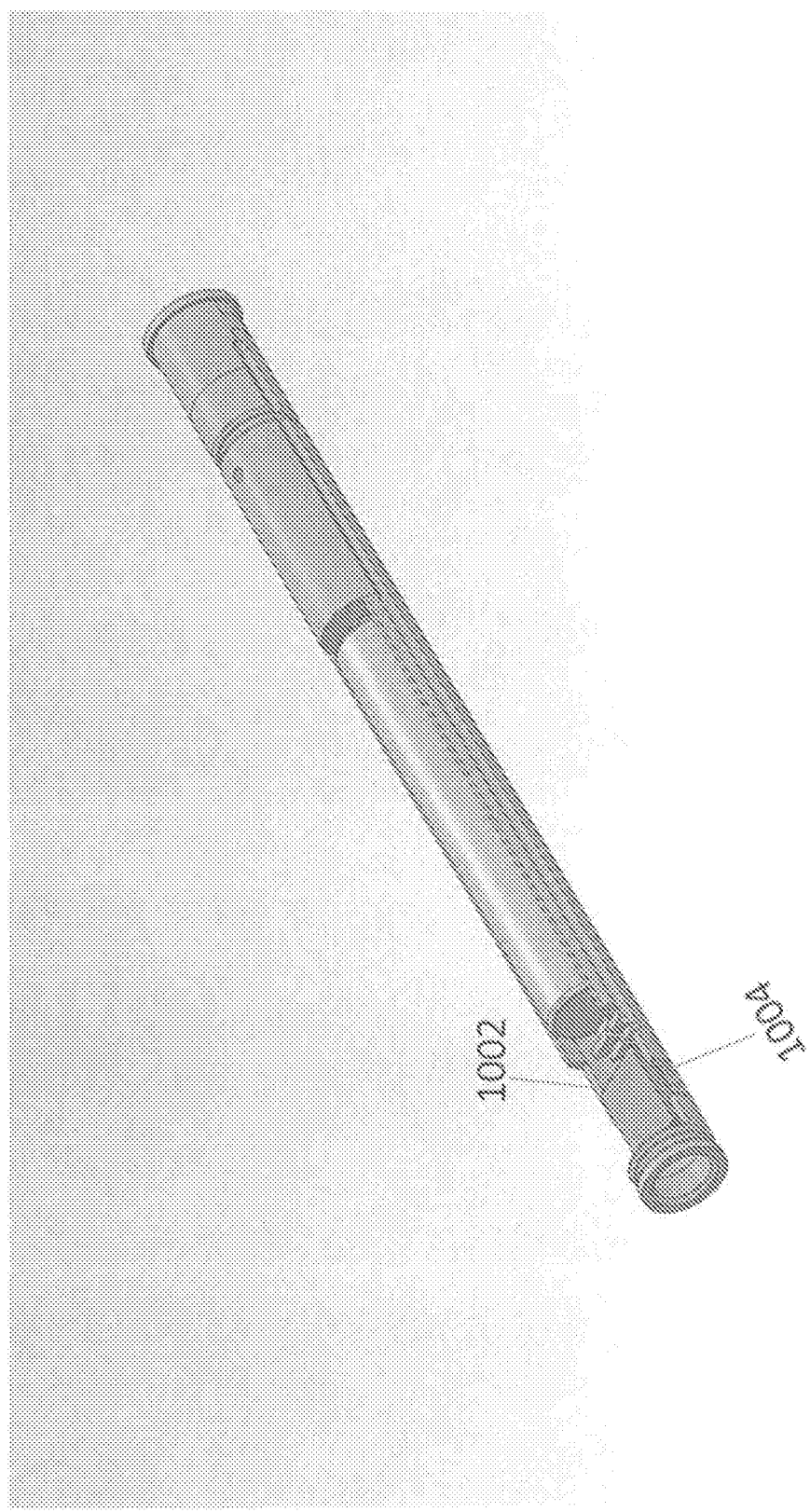
Figure 11:
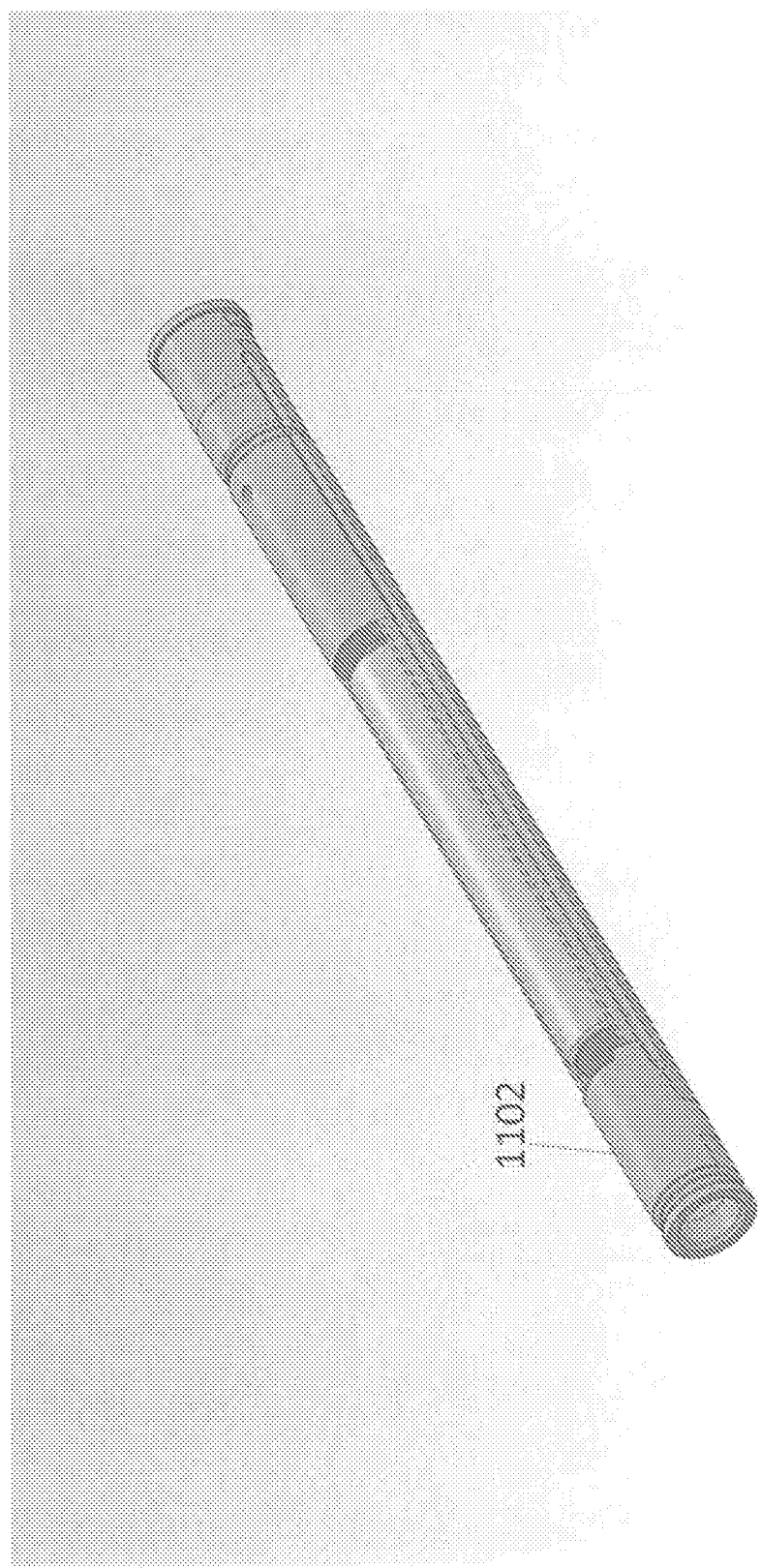

Open frame 200 may also include a slot for containing power supply unit 103, as shown in FIG. 9. For example, the slot may be configured to securely hold a power supply source such as a lithium-poly or other battery type. As shown in FIG. 10, the open frame 200 may also include a slot 1002 for containing a sensor (not shown), such as an air-flow sensor and a slot for containing a printed integrated circuit (IC) board (or chip) 1004, which may include a microprocessor and an LED indicator. In some aspects, the sensor may include sensor 132 shown in FIG. 1. A cap 1102 may be affixed (e.g., snapped in place) to the open frame 200 to securely hold the sensor and IC chip, as shown in FIG. 11.

Figure 12:
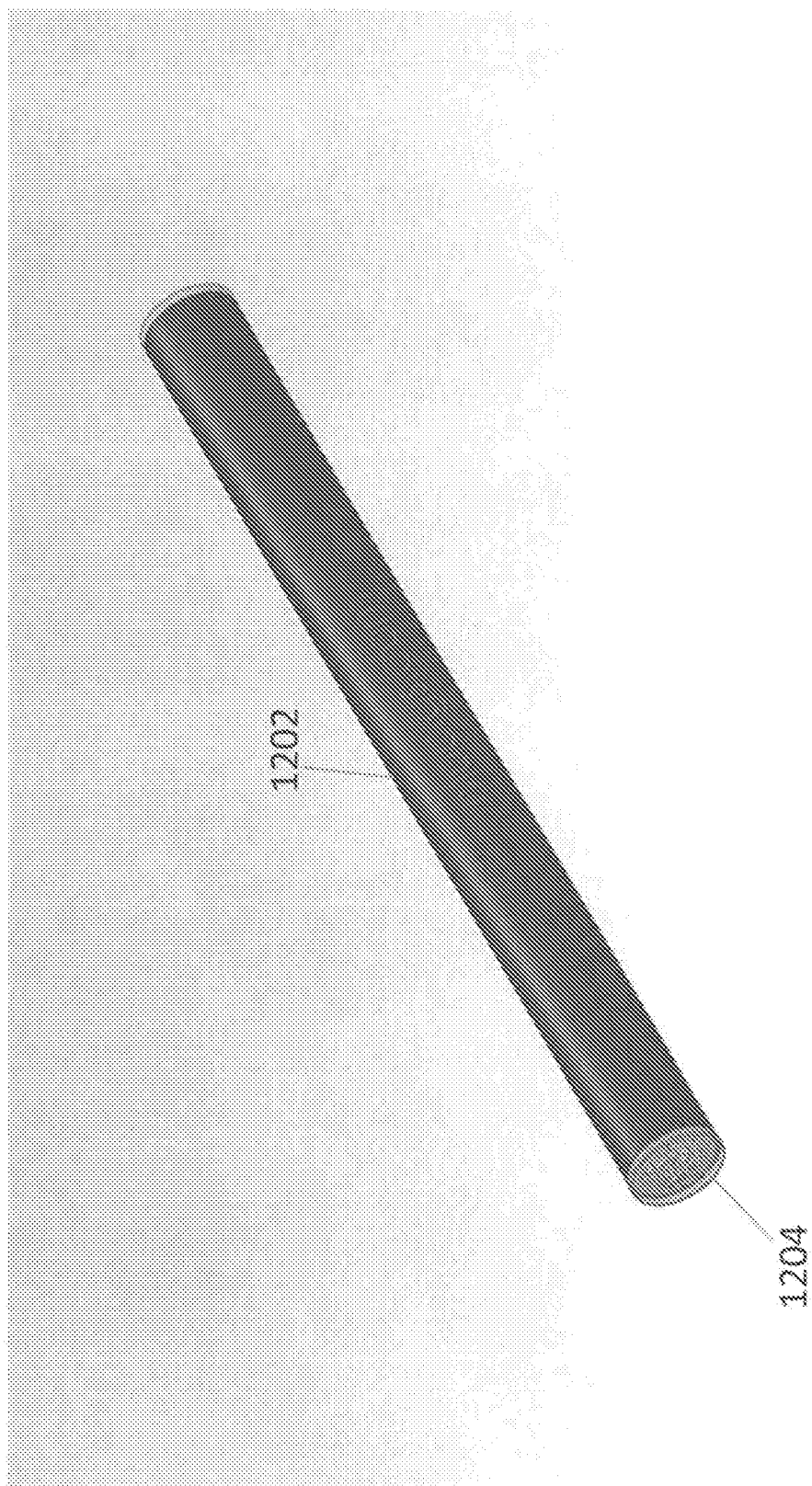

As shown in FIG. 12, an outer sleeve 1202 may be placed over or formed onto the ESD housing, which includes the open frame 200, liquid chamber cover 512, and caps 802, 1102, and battery cover (not shown). A lens cover 1204 may be placed at an end of the ESD, which may have the aesthetic appearance of ash forming on the end of a cigarette when lit. The components of the ESD, including outer sleeve 120, open frame 200, liquid chamber cover 512, caps 802, 1102, battery cover, and lens cover 1204, may be made of a material comprising, e.g., plastic, metal, foam, ceramic, glass, wood, carbon-fiber, or the like.

Figure 13:
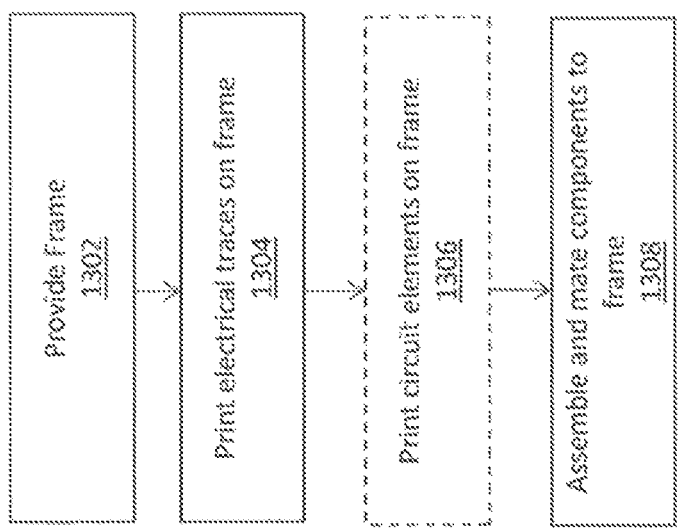
FIG. 13 shows an example of a method for manufacturing an electronic smoking device.

A method for manufacturing a modular ESD is shown in FIG. 13. As seen at 1302, a frame, such as open frame 200 may be provided. The frame may include slots configured for mating with and containing each component of the ESD. As seen at 1304, electrical traces may be printed on the frame. For example, the traces may be printed on the frame (e.g., using 3D printing). One or more circuit elements may be optionally printed on the frame, as seen at 1306. Again, 3D printing, lithography, etching, or other semiconductor processes may be used to print the circuit elements. As seen at 1308, the components of the ESD may be assembled and mated to the frame, traces, and or circuit elements, for example, in the sequence illustrated in FIGS. 2 through 12.

Figure 14:
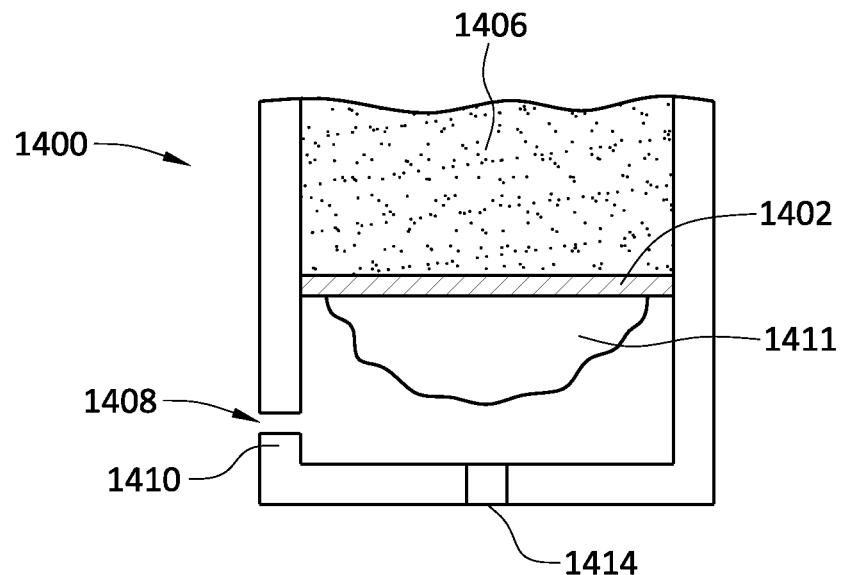
FIGS. 14-15 show partial cut-away views of two examples of heating elements that may be used with the electronic smoking device of FIGS. 1-12.

FIG. 14 shows a partial, cut-away view of another example of an ESD. ESD 1400 includes a porous ceramic heater 1402 that is in direct contact with the smoking liquid 1406. The porous ceramic heater 1402 is constructed such that droplets remain suspended in the holes in the porous ceramic heater 1402. When a negative pressure is applied to the heater 1402 (e.g., by sucking on the aerosol delivery end of the ESD), the droplets are released from the heater 1402 and emitted into the air stream 1408 injected through the air port 1410 to form an aerosol 1411 that exits through the aerosol delivery end 1414. In accordance with some aspects of the disclosure, droplets may be vaporized at the surface due to heat rather than air pressure forcing molecules off the surface. A wicking action may be performed to replenish the surface with new juice droplets.

Figure 15:
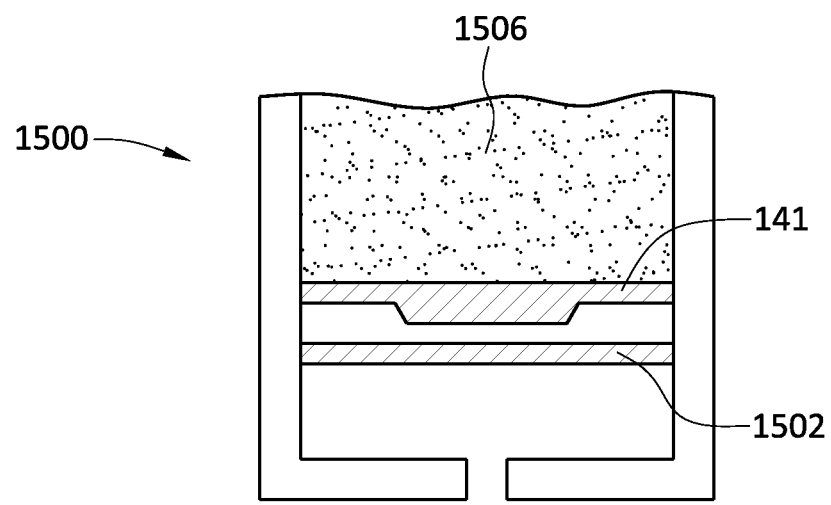

FIG. 15 shows a partial, cut-away of an example of yet another example of an ESD. ESD 1500 includes a non-porous ceramic heater 1502 that may be placed near the dispensing control device 141, which may be in direct contact with the smoking liquid 1506. In one embodiment, the non-porous ceramic heater 1502 can comprise a thin film resistor deposited onto a ceramic. The dispensing control device may include holes that have diameters constructed to hold droplets of the smoking liquid and, when a negative pressure is applied to the aerosol delivery end of the ESD, to release the droplets so that they contact the heater 1502 to form an aerosol when mixed with the air in the ESD. As described above, the ESD may be constructed as a single unit or as a combination of separable components. In accordance with some principles of the disclosure, the separable components may include a portion of the ESD containing the smoking liquid and the heater. Accordingly, a user can purchase replacements for or replenish only the consumable portion of the ESD. In accordance with some aspects of the disclosure, other portions of the ESD may also be separable.

According to a further aspect of the disclosure, a computer-readable medium is provided that includes sections or segments of code that, when executed on a computer, cause the processes described herein to be carried, such as, for example, the process of assembling the ESD, as shown in the sequence of steps in FIGS. 2-12. The computer-readable medium may include a section or segment of code to carry out each unique step described herein.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a super computer, a personal computer, a laptop computer, a palmtop computer, a notebook computer, a desktop computer, a workstation computer, a server, or the like, or an array of processors, microprocessors, central processing units, general purpose computers, super computers, personal computers, laptop computers, palmtop computers, notebook computers, desktop computers, workstation computers, servers, or the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, or the like, or any combination of the foregoing, any of which may be configured to communicate data via a wireless and/or a wired communication medium. These networks may run a variety of protocols not limited to TCP/IP, IRC or HTTP.

A "computer-readable medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications that fall within the spirit and scope of the appended claims. These examples given above are merely illustrative and are not meant to be an exhaustive list of all possible designs, embodiments, applications or modification of the disclosure.

What is claimed:

1. An electronic smoking device comprising the following:
   a frame through which an air flow path at least partially extends;
   an air inlet fluidly connected to the air flow path;
   a container for storing a smoking liquid;
   an atomizer positioned in the frame and configured to receive the smoking liquid from the container and air from the air flow path to generate a vaporized liquid;
   a circuit coupled to the atomizer;
   a conductive trace printed directly along the frame; and
   a slot included in the frame, wherein the slot is configured for mating and containing at least a portion of the container, the atomizer, or the circuit;
   wherein the atomizer is configured to be electrically connected to a power supply through the circuit and the conductive trace.

2. An electronic smoking device according to claim 1, wherein the frame comprises at least one circuit element printed directly on the frame.

3. An electronic smoking device according to claim 1, wherein the atomizer comprises a porous ceramic heater.

4. An electronic smoking device according to claim 3, wherein the porous ceramic heater comprises a thing film resistor deposited onto a ceramic.

5. An electronic smoking device according to claim 1 further comprising a dispensing control device.

6. An electronic smoking device according to claim 5, wherein the dispensing control device comprises a micro liquid screen.

7. An electronic smoking device according to claim 1 further comprising a sensor electrically connected to the power supply and to the atomizer.

8. An electronic smoking device according to claim 1 further comprising a controller electrically connected to the atomizer.

9. An electronic smoking device according to claim 1 wherein the air inlet extends from an exterior surface of the frame.

10. An electronic smoking device according to claim 1 further comprising a communication unit operably connected to the battery.

11. An electronic smoking device according to claim 10, wherein the communication unit is configured to communicate with a memory to exchange information.

12. An electronic smoking device according to claim 1 wherein the frame further comprises at least one slot configured to contain plated electrical contacts.

13. An electronic smoking device comprising the following:
   a frame through which an air flow path at least partially extends;
   an air inlet fluidly connected to the air flow path;
   a power supply positioned in the frame;
   a container for storing a smoking liquid;
   an atomizer positioned in the frame and configured to receive the smoking liquid from the container and air from the air flow path to generate a vaporized liquid;
   a conductive trace printed along the frame;
   a circuit independent of the conductive trace; and
   a slot included in the frame, wherein the slot is configured for mating and containing at least a portion of the power supply, the container, the atomizer, or the circuit;
   wherein the power supply and the atomizer are configured to be electrically connected through the circuit and the conductive trace.

14. An electronic smoking device according to claim 13 wherein the atomizer comprises a porous ceramic heater.

15. An electronic smoking device according to claim 13 further comprising a controller electrically connected to the atomizer.

16. An electronic smoking device according to claim 13 further comprising a communication unit operably connected to the battery.

17. An electronic smoking device according to claim 13, wherein the communication unit is configured to communicate with a memory to exchange information.

18. An electronic smoking device according to claim 13 wherein the frame further comprises at least one slot configured to contain plated electrical contacts.

19. An electronic smoking device comprising the following:
   a frame;
   an air flow path extending through the frame;
   an air inlet fluidly connected to the air flow path;
   an air outlet fluidly connected to the air flow path;
   a power supply positioned in the frame;
   a container for storing a smoking liquid;
   an atomizer positioned in the frame and configured to receive the smoking liquid from the container and air from the air flow path to generate a vaporized liquid;
   a circuit coupled to the atomizer; and
   a slot included in the frame, wherein the slot is configured for mating and containing at least a portion of the power supply, the container, the atomizer, or the circuit;
   wherein the power supply and the atomizer are configured to connect through the circuit and wherein one or more traces of the circuit are printed directly on the frame.

20. An electronic smoking device according to claim 19 wherein the frame further comprises at least one slot configured to contain plated electrical contacts.

* * * * *